United States Patent
Laversanne et al.

(10) Patent No.: US 6,277,404 B1
(45) Date of Patent: Aug. 21, 2001

(54) METHOD FOR MAKING A PRODUCT ADHERE TO A SURFACE

(75) Inventors: René Laversanne, Pessac; Corinne Degert, Saint Medard en Jalles; Didier Roux, Merignac, all of (FR)

(73) Assignee: Capsulis, Pessac (FR)

( * ) Notice: Subject to any disclaimer, the term of this patent is extended or adjusted under 35 U.S.C. 154(b) by 0 days.

(21) Appl. No.: 09/402,458

(22) PCT Filed: Apr. 10, 1998

(86) PCT No.: PCT/FR98/00729

§ 371 Date: Oct. 8, 1999

§ 102(e) Date: Oct. 8, 1999

(87) PCT Pub. No.: WO98/46199

PCT Pub. Date: Oct. 22, 1998

(30) Foreign Application Priority Data

Apr. 14, 1997 (FR) .................................................. 97 04548

(51) Int. Cl.⁷ .................................................. A61K 9/127
(52) U.S. Cl. ............................................. 424/450; 424/400
(58) Field of Search ............................................. 424/450

(56) References Cited

U.S. PATENT DOCUMENTS 5,264,618  11/1993  Felgner et al. ........................ 560/224
5,610,201  * 3/1997  Grollier et al. ...................... 514/773

FOREIGN PATENT DOCUMENTS

| 0457910 | 11/1991 | (EP) . |
| 59-210013 | 11/1984 | (JP) . |
| 90/06747 | 6/1990 | (WO) . |
| 92/19214 | 12/1992 | (WO) . |
| 93/19735 | * 10/1993 | (WO) . |
| 95/23578 | 9/1995 | (WO) . |
| 96/31196 | 10/1996 | (WO) . |

* cited by examiner

*Primary Examiner*—Jose' G. Dees
*Assistant Examiner*—Konata M. George
(74) *Attorney, Agent, or Firm*—Dennison, Scheiner, Schultz & Wakeman

(57) ABSTRACT

Method of making a product adhere to a surface, in which a composition is brought into contact with the surface, the composition containing the product incorporated in substantially spherical, multilamellar vesicles, with a diameter of between 0.1 and 100 μm, and including concentric membranes based on at least one surfactant and separated by a solvent medium. Each of the vesicles has an onion-like structure formed of a succession of concentric bi-layers extending from each vesicle center to its periphery, and containing therein at least one cationic agent, resulting in the vesicles carrying a positive overall charge.

13 Claims, No Drawings

METHOD FOR MAKING A PRODUCT ADHERE TO A SURFACE

BACKGROUND OF THE INVENTION

The present invention relates to a method of making a product adhere to a surface.

It further relates to the applications of such a method in different fields depending on the nature of the surface and that of the product.

It is very particularly applicable to the treatment of biological surfaces such as human skin or hair, animal skin or fur or the cuticle of plants or insects.

It is also applicable to the treatment of fibers, both natural and artificial, and to fiber-based products such as fabrics.

Different fields of industry are known where it is sought to improve the interaction between a product and a surface or to fix a product to a surface, either in order to improve the state of this surface or in order to subject it to a particular treatment. Particular possible applications are those where it is sought to modify the properties of a surface by subjecting it to a particular treatment with a product which needs to remain in contact with this surface for a sufficiently long time.

It is often useful to be able to treat fibers or textile or natural surfaces in order to improve their appearance (brightness, color, fragrance, etc.) or their properties (wear resistance, elasticity, slip, etc.) or in order to give them new functions.

In the case of skin, body hair/fur and hair, it is often sought to apply active agents thereto which medicate, treat or fortify it, for example.

In general terms, "active agent" or "active product" will be used indiscriminately below to denote the product which it is desired to fix to a surface.

One of the problems encountered in these various treatments is to ensure that the product persists on the surface, whether it be an inert surface or a biological surface such as the skin, body hair/fur, hair or integuments of living beings or the surface or cuticle of plants. Very often, the treatment is applied by means of a chemical reaction or by physico-chemical adsorption (for example dyeing) during the manufacture of the fiber, or by means of a treatment requiring a special application in the case of human hair.

If an attempt is made to apply the treatment during a washing operation or when shampooing, for example, the main problem encountered is the fact that the active agent delivered by the shampoo or the detergent product, which is rinsed off, is very largely lost, only a tiny fraction remaining fixed to the treated surface. The persistence is therefore low, even if the proportion of active agent in the product is high. The same type of problem can arise if the treated surface is then exposed to the action of rain, for example.

Microencapsulation is a solution commonly used to prolong the period of availability of an active agent by only releasing it slowly. It is usually effected by forming a polymer shell around the active principle, either by spraying the active agent in the presence of a polymer or by one of the numerous encapsulation methods developed in industry, such as the various techniques of coacervation, atomization and coprecipitation. Liposomes can also be used, but their low stability and their cost prevent them from being used industrially.

International patent application WO 95/23578 describes the use of cationic liposomes for depositing an active ingredient on hair. The main problem presented by such liposomes is that the technique used to prepare them, which is simply to add the components of the liposomal membrane to the solution of active agent, does not easily allow control over the degree of encapsulation, which in any case is always low. Furthermore, only water-insoluble active agents can be encapsulated in such liposomes, thereby considerably limiting the list of active products suitable for use in such a technique.

SUMMARY OF THE INVENTION

It has now been discovered that, provided they are formulated so as to have a positive overall charge, multilamellar microcapsules of onion-like structure, also called microvesicles or multilamellar vesicles below, possess the property of fixing themselves in a particularly stable manner to different surfaces and more particularly to the surface of natural or synthetic fibers or products based on such fibers, or to hair or to body hair/fur.

Multilamellar vesicles of "onion-like" structure are understood as meaning multilamellar vesicles of substantially spherical shape which consist of a series of concentric bilayers from the center to the periphery of the vesicles, which is why the term onion-like structure is used by analogy to qualify such structures.

These structures can be demonstrated by microscopic examination of the compositions. They are observed under a polarized light microscope, showing a birefringent lamellar phase. This exhibits a characteristic texture associated with the presence of defects (grain boundaries) between the differently orientated phase domains. In the case of the concentrated phase of vesicles, the texture is characterized by its fine uniform character relating to the size of the vesicles. In the disperse phase of vesicles, the latter are visible in the form of slightly birefringent dots of greater or lesser resolution (according to the size). The birefringence is observed only when the dispersion is not too dilute. Therefore, if the dispersion is relatively dilute, it will be necessary to concentrate it beforehand in order clearly to show the birefringence characteristic of the presence of the vesicles of onion-like structure.

It is quite obvious that in the present case, as in the case of the cationic liposomes described in international patent application WO 95/23578, the cationic charge on the liposomal entity or microcapsule is compensated at equilibrium by counterions. However, this charge can be demonstrated by measurements of zeta potentials made on a zeta meter. Such experiments are based on measurements of mobility in the presence of an electric field.

DETAILED DESCRIPTION OF THE INVENTION

The vesicles used according to the invention can be obtained in a particularly simple manner by forming a lamellar liquid crystal phase and causing the bilayers formed to rearrange into multilamellar vesicles. A process of this type, affording microcapsules of controlled size, is described in international patent application WO 93/19735; said document describes a process which, through the use of a step involving homogeneous shearing of a lamellar liquid crystal phase, makes it possible to prepare microcapsules of controlled size, not only from lipidic surfactants capable of forming liposomes, but also from various anionic or nonionic surfactants, and proposes the encapsulation of substances, especially biological substances, in these capsules.

International patent application WO 95/19707 in turn describes a process for improving the persistence of an odor, which consists in encapsulating an odoriferous active principle inside a microcapsule consisting of a multilamellar arrangement of concentric bilayers separated by an aqueous medium. These microcapsules are obtained by preparing a liquid crystal phase or a liquid crystal phase suspension from at least one surfactant and causing the bilayers to rearrange into microcapsules. This rearrangement can be brought about in particular by using the process described in international patent application WO 93/19735 cited above.

According to the invention, the active product which is to be made to adhere to a surface from a composition is almost totally incorporated inside multilamellar vesicles, which will be indiscriminately called microcapsules, microvesicles or vesicles in the present specification. These microcapsules are advantageously of substantially spherical shape and consist of concentric lamellae, giving them a structure of the "onion" type.

The active substance is thus included right inside the microcapsule, generally in its membranes, and, if appropriate, if it is purely hydrophilic, in the water or the interstitial liquid included inside the microcapsule. However, it always forms an integral part of the microcapsule.

Even though water/surfactant media are generally used to produce the microcapsules of the invention, replacement of the water with a polar solvent, for example glycerol, is in no way excluded.

According to another advantage, the technology proposed according to the invention makes it possible to prepare vesicles which have a very high encapsulation yield, especially a yield in excess of 90% and generally very close to 100%. Being easy to use, this technology also makes it possible to prepare large quantities of encapsulated products. In addition, it does not involve an organic cosolvent, so all kinds of industrial applications can be envisaged, particularly in fields where the use of organic solvents is banned. This constitutes a very particular advantage in the cosmetic, pharmaceutical or food industry, where it is sought to avoid as far as possible the use of organic solvents, which are often difficult to remove completely. However, it is also of value in other sectors of industry where the current tendency is to replace organic solvents with aqueous media.

Another advantage derives from the fact that the use of surfactants imparts a good dispersibility to the formulation, which can be used in liquid form in aqueous dispersion. This feature is particularly advantageous in the case of hydrophobic or water-insoluble molecules, which can be dispersed by virtue of the invention without the need for an organic solvent.

Cationic agent is understood as meaning a product carrying a positive charge.

According to one of its essential characteristics, the invention relates to a method of making a product adhere to a surface, characterized in that it consists in bringing into contact, with said surface, a composition in which said product is incorporated in substantially spherical, multilamellar vesicles, with a diameter of between 0.1 and 100 $\mu$m, consisting of concentric membranes based on at least one surfactant and separated by a solvent medium, said vesicles having an onion-like structure and carrying a positive overall charge due to the presence of at least one cationic agent inside said vesicles.

The multilamellar vesicles whose use is claimed in the present patent application make it possible to encapsulate a large number of active agents with a very good yield. In addition, the composition of the mixture of surfactants making up the membranes of the vesicles can be adapted to the envisaged application and these vesicles can be prepared from all classes of surfactants.

The invention is very particularly applicable to the fixing of a product to a surface which has a negative charge, as is the case of the majority of natural surfaces as well as a large number of artificial surfaces, particularly fibers, body hair/fur, hair, skin, integuments and the cuticle of plants and insects.

According to one of its essential features, the invention relates to the treatment of a natural or artificial fiber or an assembly of fibers, such as a fabric, for the purpose of fixing an active agent thereto.

According to another particularly important feature of the invention, the surface to be treated will be a biological surface, particularly an external part of the human or animal body, such as the skin, integuments, body hair/fur, hair or cuticle, or the hairs of insects, or an aerial part of plants, particularly their cuticle.

In one particular variant, the treatment may be a cosmetic or hygiene treatment for the human or animal body which is intended especially to increase the persistence of an active agent on the treated part of the body, said treatment involving the application of a cosmetic or hygiene composition in which said active product is incorporated in substantially spherical, multilamellar vesicles, with a diameter of between 0.1 and 100 $\mu$m, consisting of concentric membranes based on at least one surfactant and separated by a solvent medium, said vesicles having an onion-like structure and carrying a positive overall charge.

Of course, the nature of the product to be fixed will depend closely on the surface to be treated and the intended result. However—and this constitutes one of the essential advantages of the invention—the microcapsules used according to the invention to bring the product into contact with the surface make it possible, by virtue of their nature and preparative process, to incorporate therein a practically unlimited number of products which it is desired to fix to the surface to be treated. This further constitutes a great advantage of the invention, particularly compared with the techniques involving liposomes. In fact, it is well known to those skilled in the art that, because of the manufacturing technology, liposomes can only contain a limited number of encapsulated products.

The vesicles used according to the invention must have a positive overall charge.

Said charge can be imparted either by choosing the nature of the surfactants used to manufacture the microcapsules, or by encapsulating an agent of cationic character inside the microcapsule.

It should be noted that, as is apparent from the following description, the possibility that the agent of cationic character imparting the positive charge to said vesicle may consist of one of the surfactants making up the vesicle membranes or, if appropriate, the product which it is desired to fix in the method of the invention, can in no way be ruled out.

As is apparent from the following description, but also from the inventors' publications, in particular in international patent application WO 97/00623, the multilamellar vesicles which can be used according to the invention advantageously contain two surfactants in their membranes. The experiments performed by the inventors show that the surfactants forming part of the composition of said vesicles do not necessarily have to be all cationic for the overall charge on the vesicle to be positive and sufficient for assuring the desired fixing. In fact, when they are associated with the presence of a cationic surfactant, the desired overall positive charge and the desired effect are advantageously achieved at cationic surfactant concentrations which represent 0.01 to 10% by weight of the multilamellar vesicle.

The following may be mentioned, without implying a limitation, as cationic surfactants which can be used according to the invention:

quaternary ammonium compounds, in which the counterion can be:
chloride, bromide, phosphate, hydroxide, methosulfate, sulfate or a carboxylic acid anion, and in which the substituents on the nitrogen can be:
optionally hydroxylated, saturated or unsaturated alkyl chains having 1 to 20 carbons, it being possible for the hydroxyl group to be esterified and it being possible for these chains to be substituted, to originate from defined compounds or to be mixtures derived from natural products,
optionally substituted aromatic groups,
optionally substituted rings, particularly aromatic rings, for example pyridine,
mixtures of these various categories, or
themselves substituted by a quaternized or non-quaternized amine group;
amines, which can be protonated according to the pH, and amine salts, in which the nitrogen carries the abovementioned substituents and/or hydrogen, these products being used under conditions where they are cationic;
amide derivatives, which can be protonated according to the pH and are optionally substituted by the abovementioned groups, these products being used under conditions where they are cationic;
betaine or amino acid derivatives under pH conditions which render them cationic, these derivatives optionally being substituted by the above-mentioned groups; and
quaternized dialkyl esters.

A cationic polymer will advantageously be used as the encapsulated cationic agent for imparting a positive charge to the vesicle.

The following may be mentioned as examples of such polymers:

naturally cationic or quaternized polysaccharide derivatives of natural, biotechnological or synthetic origin;
cationic protein hydrolyzates;
polyamine derivatives optionally substituted by polyethylene glycol members;
polyamino acids under pH conditions where they are cationic; polyethylene imine;
quaternized derivatives of polyvinylpyrrolidone (PVP) and copolymers of quaternized polyvinylpyrrolidone and hydrophilic polymers (urethane, acrylate, etc.);
polyquatemium compounds, which are cationic polymers described in the International Cosmetic Ingredient Dictionary published by the CTFA (Cosmetic, Toiletry and Fragrance Association); and
chitin derivatives.

It has been found that a small amount of cationic components (encapsulated cationic surfactants and/or agents, particularly cationic polymer) is sufficient to assure the adhesion of the vesicles to the surface. More precisely, the multilamellar vesicles of the invention advantageously contain from 0.01% to 10% by weight, preferably from 0.1% to 5% by weight, of said cationic agent, based on the total weight of the vesicle composition.

As seen above, the choice of product to be fixed depends closely on the surface to be treated. The possibility that, in certain cases, the product to be fixed may consist either of one of the cationic surfactants or of the encapsulated cationic agent, for example a cationic polymer, is not ruled out.

This is the case particularly of the use of cationic polymers when it is desired to cover human or animal hair, as is well known in the field of cosmetics or hygiene. In this case, the product to be fixed may be the polymer itself, which will act both as the cationic agent imparting a positive overall charge to the multilamellar vesicle, and as the product to be fixed.

It is also the case when the active product can consist of a cationic surfactant, for example a quaternary ammonium compound, which may be used both as a bactericide to treat a surface, and as a constituent of the vesicle membranes.

The scope of the treatments to which the invention relates also extends to topical pharmaceutical or veterinary treatments of human skin or hair as well as animal skin or fur.

The invention therefore further relates to methods in which it is sought to fix, to the human or animal body, a pharmaceutical composition comprising an active agent incorporated in a pharmaceutically acceptable vehicle. It relates in particular to a pharmaceutical composition for the treatment of the human or animal body in which at least one active agent forms an integral part of microvesicles as described above.

As seen above, one of the advantages of the present invention is that it provides a particularly flexible technique for the preparation of compositions incorporating a product which it is desired to fix to a surface.

In fact, the compositions for carrying out the method described above, or the pharmaceutical compositions as described above, are easily prepared from a lamellar liquid crystal phase based on at least one surfactant comprising a cationic agent and, if appropriate, a product to be fixed or an agent other than said cationic agent, by shearing said lamellar liquid crystal phase to form said vesicles, and then incorporating said vesicles into a suitable medium.

This medium will of course be chosen according to the intended application of the composition containing the cationic vesicles. In particular, it may be an aqueous, oily or organic medium. In each case, the formulation of the multilamellar vesicles will of course be adapted according to the nature of the dispersion medium.

Thus for example, in the field of human or animal cosmetics or hygiene, the compositions incorporating the vesicles will advantageously be in the form of aqueous lotions, shampoos, emulsions, gels, oily dispersions, balms, aerosol solutions or formulations for transdermal applications.

The multilamellar vesicles may be dispersed in an aqueous medium.

The cationic multilamellar vesicles may also be dispersed in a lipophilic medium, for example an oil or a mixture of wax and oil. Such media may prove particularly valuable, especially in all the fields of application where it is sought to make an active principle adhere to human or animal skin, hair, body hair/fur. Examples of such fields which may be mentioned in particular are that of cosmetic products, for example make-up products such as mascara and lipstick, or that of non-alcoholic body deodorants comprising a stearic gel or a silicone oil as excipient.

Another field of application where it may be advantageous to use cationic vesicles dispersed in a lipophilic medium is that of treatments applied topically to an animal's skin. Such treatments are commonly referred to as "pour-on" treatments and consist in spreading a composition with a topical effect over the animal's fur.

The cationic component, particularly the cationic surfactant or polymer, is introduced into the composition of the lamellar phase before the latter is sheared to form the vesicles. It is therefore co-encapsulated with the active agent, inside the vesicle, and forms an integral part thereof The formulation of the surfactants is adapted to take account of the presence of the cationic surfactant and/or cationic polymer.

Of course, the nature of the active products which can be used as products to be fixed to a surface depends on the type of surface and the intended treatment.

Examples of the active agents which can be used are those used in cosmetics for treating hair or for hygiene treatments on the human or animal body, but also those used in human or veterinary pharmacy for topical applications, as well as those used in the textile industry.

The following active agents may be mentioned as examples in the field of cosmetics and human and veterinary pharmacy:

essentially water-soluble active agents such as extracts of plants or algae, vitamins, water-soluble proteins, protein hydrolyzate, peptides, α-hydroxy acids, salicylic acid, caffeine derivatives, and moisturizing products such as glycerol or glycol derivatives; and essentially liposoluble active agents such as vegetable and animal oils, synthetic hydrocarbon or silicone oils, essential oils and mixtures thereof, perfumes and flavorings, vitamins and fatty acid derivatives.

Other active products can also advantageously be encapsulated in order to improve their adhesion to a surface to be treated; the following may be mentioned in particular:

bactericides such as triclosan derivatives, quaternary ammonium compounds, zinc derivatives (zinc pyrithione, zinc undecylenate), piroctone olamine, etc.

The invention is also very particularly applicable to all applications where it is sought to improve the fixing of an insecticide to a target. Insecticides, and particularly the following:

pyrethrin and synthetic pyrethrinoids (permethrin and derivatives);

phosphorus compounds, for example malathion and parathion; and organochlorine compounds, for example lindane, may therefore also be mentioned as active products to be fixed.

Among the preferred targets intended as surfaces within the framework of the method of the present invention, plants and insects may be mentioned very particularly.

Plants and insects are enclosed in a membrane analogous to skin, called a cuticle, although its nature differs from insects to plants. The cuticle of insects is a hard layer of keratin (analogous to the keratin of human hair). In general it is at least partially covered with hairs having a tactile, sensory or motor effect; these hairs are called integuments and their chemical nature is analogous to that of the cuticle. These are therefore preferred surfaces for adhesion of the vesicles of the invention. Fixing such vesicles directly to the cuticle or hairs of the insect is capable of boosting the action of the insecticides by prolonging the duration of their contact with the insect. This is particularly important in the case of treatments on humans or animals, such as treatments for combating parasites, acarids or lice, where on the one hand it is sought to reduce the dose of insecticide employed, and on the other hand the products are rarely associated with shampoos because they are removed during rinsing.

As far as plants are concerned, the same adhesion mechanisms can be employed. The usefulness of said adhesion is again obvious because, when plants are treated, they are naturally rinsed by the effect of rain. It is therefore very important to retain the maximum amount of active substance on the cuticle in order to obtain the desired surface action, particularly in the case of surface insecticides and fungicides.

In another variant, the invention further relates to a method of preparing the compositions used according to the invention. This method consists in preparing a lamellar liquid crystal phase containing at least one surfactant, a polar solvent, which advantageously consists of water, and, if appropriate, at least one product or composition which it is desired to encapsulate, and in causing said liquid crystal phase to rearrange into multilamellar vesicles.

For the reasons given above, the presence of another product or composition is not always obligatory insofar as this can be the cationic surface-active product which, in one variant of the invention, can act both as the agent imparting the cationic charge and as the product to be fixed according to the invention.

In the present case, the formulation of the lamellar phase is such that at least one of the following conditions is met:

at least one of the surfactants is a cationic surfactant;

a cationic product is incorporated in said lamellar phase.

More precisely, the preparative technique consists in a first step in preparing a lamellar liquid crystal phase containing a mixture of the surfactant(s), the polar solvent, which is preferably water, and, if appropriate, the active product or mixture which it is sought to encapsulate, and then in shearing said liquid crystal phase to form the multilamellar vesicles.

To optimize the encapsulation yield, the chosen conditions will be such that the liquid crystal phase is homogeneous, i.e. a monophase, so that the polar solvent (generally water) and the active product or mixture are solubilized together in this lamellar phase.

The optimum conditions to be used may generally be determined by examining a series of compositions containing variable amounts of solvent and active product This examination will be carried out either by macroscopic observation of the phase separation or by microscopic observation under a light microscope, preferably a polarizing microscope.

However, the formation of a liquid crystal phase is not a sufficient condition for the subsequent production of a readily dispersible suspension of multilamellar vesicles. It is also necessary to organize this lamellar phase into a compact stack of these vesicles. This rearrangement may be effected by applying a homogeneous shearing stress, as described in patent application WO 93/19735. This rearrangement may also be effected by varying the particular formulation of the mixture, especially by choosing a mixture of surfactants such that the desired texture, in the form of multilamellar vesicles, forms spontaneously or, failing that, when a simple mechanical stress is applied, for example when the products are mixed, which causes said mechanical stress.

It is for this reason that the mixture of surfactants and the respective concentrations of each of the surfactants contained in this mixture will advantageously be chosen so as to give the desired texture.

More precisely, the mixture of surfactants used will generally consist of two types of surfactants, the one rather being soluble in water and therefore having a high HLB, and the other rather being soluble in oil and therefore having a relatively low HLB. Furthermore, it will be particularly advantageous for at least one of the surfactants to have a relatively low CMC, preferably of less than $10^{-5}$ mol/liter and particularly preferably of less than $10^{-6}$ mol/l.

The proportion by weight of surfactants in the final mixture is generally between 5 and 90% and preferably between 30 and 70%.

More precisely, the starting mixtures used to obtain the desired microcapsules will have the following properties:

1) The mixture must form a homogeneous, lamellar liquid crystal phase for proportions by weight of water ranging from 10 to 98% and more generally from 20 to 60%.

2) This homogeneous lamellar phase must have a specific texture, i.e. a spatial arrangement of the lamellae which corresponds to an "onion-like" structure, either spontaneously, or on simple mixing, or under the action of a specific shearing stress as described in international patent application WO 93/19735. This structure can easily be recognized by those skilled in the art with a polarizing microscope.

To satisfy the above two conditions, it will be advantageous, as explained above, to use two surfactants with substantially different hydrophilic/lipophilic balances so that the organizational (textural) properties of the lamellar phase can be regulated at will.

The preferred choice will be to mix a rather lipophilic surfactant with a low HLB of between 3 and 7 and a hydrophilic surfactant with a high HLB of between 8 and 15. By varying the proportions of the two types of surfactants, those skilled in the art will easily be able to obtain a homogeneous lamellar phase with the desired textural properties.

The two types of surfactants will be selected from those which are compatible with the intended use.

Depending on the formulation of the lamellar liquid crystal phase and, more precisely, depending on the nature and/or proportions of the surfactants used, application of the preparative method described above ultimately gives two types of vesicles which differ from one another by the degree of organization of the surfactant molecules in the membrane forming the compartments of the multilamellar vesicles:

The vesicles of the "fluid" type correspond to membranes in which the surfactant molecules are free to move and are not organized in the form of a two-dimensional crystal lattice. They are generally of spherical shape.

By contrast, the vesicles of the "solid" type correspond to an organization of the surfactant molecules in the form of a two-dimensional crystal lattice. These vesicles are of anisotropic shape and most frequently take the form of small faceted crystals. In all cases, the size of the vesicles is between 0.1 and 100 µm. The faceted appearance of these vesicles is not inconsistent with their onion-type multilamellar structure.

EXAMPLES

Example 1

Shampoo

Multilamellar vesicles of surfactant are prepared from the following formulation:

| | |
|---|---|
| Sorbitan stearate | 25% |
| Polysorbate 60 | 20% |
| Jaguar C13S | 5% |
| Aqueous solution of water-soluble active agents | 50% |

Water-soluble active agents which can be used are a-hydroxy acids, salicylic acid, vitamin C, caffeine, proteins (total or hydrolyzed), peptides, etc. Jaguar C13S from Rhône-Poulenc is a quaternized derivative of guar flour.

The constituents are mixed at 50° C., then cooled, with constant mechanical stirring, and then dispersed in a shampoo base formed of 15% of sodium lauryl ether sulfate in water, at a rate of 3% of vesicles in the shampoo base. The suspension is homogeneous and milky because of the presence of the light-diffusing vesicles.

For the adhesion tests, a tuft of hair is dipped in the shampoo solution containing the microcapsules, then rinsed with running water and then dried in the air. The observation is made on the dried hairs by scanning electron microscopy under a vacuum of $10^{-7}$ Torr, after the sample has been metallized.

The negatives produced at a magnification of 2500 clearly show the presence of the vesicles stuck to the hair with a uniform distribution over the surface of the hair.

Furthermore, the negatives produced at a magnification of 6000 clearly show that the vesicles adhere strongly to the surface of the hair, which they literally "wet".

Example 2

Composition for Combating Lice

Multilamellar microvesicles encapsulating malathion as an insecticide are prepared from the following formulation:

| | |
|---|---|
| Polysorbate 60 | 25 g |
| Sorbitan stearate | 32 g |
| Jaguar C13S | 3 g |
| Malathion | 10 g |
| Buffered water (pH = 6) | 30 g |

The vesicles are obtained by mixing (conical flask, mechanical stirring) the surfactants and the water at room temperature and then by heating at 60° C., with continued stirring. When the mixture is homogeneous, the heating is stopped but stirring is continued; then, as soon as the temperature has fallen below 45° C., the malathion is added and the mixture is cooled, with stirring.

This gives a homogeneous paste formed of a compact stack of lamellar microvesicles, which can be identified by observation of the characteristic texture by polarized light microscopy.

This paste is dispersed by the slow addition of buffered water at room temperature, with stirring. The final mixture contains 5% of vesicles, i.e. 0.5% of malathion. Its viscosity can be adjusted by adding a viscosity enhancer, for example Jaguar C13S or Jaguar C162 (of the same chemical nature as C13S). A proportion of 0.2% of viscosity enhancer is sufficient to give a readily applicable product.

This formulation has two advantages. On the one hand, it makes it possible to use malathion in an aqueous base while at the same time preserving the stability of the malathion, which is not known to be stable in aqueous media. On the other hand, it enables the vesicles to attach themselves to hair and to the integuments of insects, thereby giving the product a long duration of action, even after rinsing.

Said attachment aspect can be visualized by scanning electron microscopy under a vacuum of $10^{-7}$ Torr, after slight metallization, on a sample of lice-infested hair treated with the product (application by massage of the scalp for 5 min, followed by rinsing with water). The vesicles are visible both on the hair and on the insects.

Example 3
Composition for Combating Cockroaches

Multilamellar microvesicles encapsulating tetramethrin and cypermethrin as insecticides are prepared from the following formulation:

| | |
|---|---|
| Polysorbate 60 | 40 g |
| Sorbitan stearate | 5 g |
| Noramium M2SH* | 5 g |
| Tetramethrin | 5 g |
| Cypermethrin | 5 g |
| Water | 40 g |

*dialkyldimethylammonium chloride with alkyl chains derived from tallow, manufactured by CECA.

The vesicles are obtained by mixing (conical flask, mechanical stirring) the surfactants and the water at room temperature and then by heating at 60° C., with continued stirring. When the mixture is homogeneous, the heating is stopped but stirring is continued; then, as soon as the temperature has fallen below 45° C., the active molecules are added and the mixture is cooled, with stirring.

This gives a homogeneous paste formed of a compact stack of lamellar microvesicles, which can be identified by observation of the characteristic texture by polarized light microscopy.

This paste is dispersed by the slow addition of water at room temperature, with stirring. The final mixture contains 5% of vesicles, i.e. 0.25% of tetramethrin and 0.25% of cypermethrin.

The dispersion is in the form of a milk which is very effective against crawling insects. The surface fixing effect is utilized for fixing both to the insect and to the ground to give a long-term action.

Example 4
Composition for Combating Ants

Multilamellar microvesicles encapsulating permethrin as an insecticide are prepared from the following formulation:

| | |
|---|---|
| Polysorbate 60 | 35 g |
| Sorbitan stearate | 10 g |
| Dehyquart AU56* | 5 g |
| Permethrin | 12 g |
| Water | 38 g |

*bis(acyloxyethyl)hydroxyethylmethylammonium methosulfate manufactured by HENKEL.

The vesicles are obtained by mixing (conical flask, mechanical stirring) the surfactants and the water at room temperature and then by heating at 60° C., with continued stirring. When the mixture is homogeneous, the heating is stopped but stirring is continued; then, as soon as the temperature has fallen below 45° C., the active molecule is added and the mixture is cooled, with stirring.

This gives a homogeneous paste formed of a compact stack of lamellar microvesicles, which can be identified by observation of the characteristic texture by polarized light microscopy.

This paste is dispersed by the slow addition of water at room temperature, with stirring. The final mixture contains 4% of vesicles, i.e. 0.48% of permethrin.

The dispersion is in the form of a milk and is very effective against ants. This efficacy results from fixing both to the insect, which provides the immediate efficacy, and to the ground, which provides a long-term action. Tests in the natural environment showed that, when sprayed directly on top of an ants' nest, this product destroyed it in the long term (for an entire season) and prevented reinfestation.

Example 5
Fixing to a Textile Fiber

Multilamellar microvesicles are prepared from the following formulation:

| | |
|---|---|
| Polysorbate 60 | 20 g |
| Sorbitan stearate | 25 g |
| Jaguar C13S | 5 g |
| Preservative | 0.8 g |
| Water | 49.2 g |

The vesicles are obtained by mixing (conical flask, mechanical stirring) the surfactants and the water at room temperature and then by heating at 60° C., with continued stirring. When the mixture is homogeneous, the heating is stopped and the mixture is cooled, with continued stirring.

This gives a homogeneous paste formed of a compact stack of lamellar microvesicles, which can be identified by observation of the characteristic texture by polarized light microscopy.

This paste is dispersed by the slow addition of water at room temperature, with stirring. The final mixture contains 5% of vesicles. Its viscosity can be adjusted by adding a viscosity enhancer, for example Jaguar C13S, at a maximum concentration of 2%.

The very good adhesion of the vesicles to textile fibers can be visualized by scanning electron microscopy under a vacuum of $10^{-7}$ Torr, after slight metallization, on samples of different kinds of textile fibers treated by being dipped in the dispersion of vesicles and then rinsed with water.

The vesicles are visible on the fibers, whether they be made of polyamide, polyester or cotton.

Example 6
Fixing to a Fabric

Multilamellar microvesicles encapsulating a perfume are prepared from the following formulation:

| | |
|---|---|
| Polysorbate 60 | 22 g |
| Sorbitan stearate | 25 g |
| Jaguar C13S | 3 g |
| Floral Sweet* perfume | 10% |
| Preservative | 0.8 g |
| Water | 39.2 g |

*perfume supplied by Haarman & Reimer

The vesicles are obtained by mixing (conical flask, mechanical stirring) the surfactants and the water at room temperature and then by heating at 60° C., with continued stirring. When the mixture is homogeneous, the heating is stopped, the perfume is added as soon as the temperature has fallen below 45° C., and the mixture is then cooled, with continued stirring.

This gives a homogeneous paste formed of a compact stack of lamellar microvesicles, which can be identified by observation of the characteristic texture by polarized light microscopy.

This paste is dispersed by the slow addition of water at room temperature, with stirring. The final mixture contains 10% of vesicles. Its viscosity can be adjusted by adding a viscosity enhancer, for example Jaguar C13S, at a maximum concentration of 0.5%.

This dispersion of "perfumed" vesicles can be used to perfume fabrics in the long term by attaching the vesicles to the textile fiber, the perfume being released slowly. A small amount of this dispersion sprayed onto a fabric imparts a fragrance which persists for several weeks.

Example 7
Non-alcoholic Body Deodorant

Body deodorants in atomizers are alcoholic solutions of perfume and bactericide. If it is desired to avoid the use of alcohol, essentially in order to avoid the irritating sensation, dispersions in a light silicone oil are used which, when it evaporates following application, gives a sensation of freshness analogous to that obtained with alcohol.

Unfortunately, not all the active agents used in deodorants are soluble in these silicone oils. On the other hand, encapsulation makes it possible to obtain a long-lasting effect of the perfume, improving the efficacy of the deodorant. For this type of application, it is necessary to formulate vesicles which are dispersible in a silicone oil medium.

Multilamellar vesicles according to the invention are prepared from the following formulation:

| | |
|---|---|
| Soya lecithin containing 20% of phosphatidylcholine | 40 g |
| Ethoxylated lauryl alcohol with 4 ethylene oxides | 10 g |
| Perfume | 18 g |
| Bactericide (Irgasan DP300 from CIBA) | 3 g |
| Jaguar C13S | 1 g |
| Water | 28 g |

The lecithin, the cationic polymer, the bactericide and 50% of the water are first mixed at room temperature to give a homogeneous paste. When the mixture is homogeneous, the ethoxylated lauryl alcohol, the perfume and the remainder of the water are added. When the addition is complete, the mixture is stirred at room temperature until a viscous paste is obtained; this can readily be dispersed in a base for a non-alcoholic deodorant atomizer.

This base is essentially composed of a light silicone oil to which aluminum salts (perspiration blockers) can be added. The vesicles are dispersed at a concentration of 10%, giving a bactericidal strength of 0.3% in the final dispersion. This non-aqueous dispersion tends to produce a sediment due to the reduced efficacy of Brownian motion in an oily medium, and needs to be shaken by hand to resuspend the vesicles before use.

Example 8
Veterinary Dermatological Formulation

The antiparasitic treatment of livestock is often carried out using a dispersion of active substance in an oily medium, which is poured over the animal's back in a single application. The active principle then diffuses over the whole of the animal by capillarity. This method, commonly called the "pour-on" method, has the advantage of being rapid to apply and of avoiding the inhalation of the active principle, both by the animal and by the person applying the treatment, which would result from spraying.

The vesicles according to the invention are particularly suitable for the dispersion of an active principle in an oil and hence for the formulation of "pour-on" forms of veterinary active principles.

The vesicles are prepared according to the following composition:

| | |
|---|---|
| Soya lecithin containing 20% of phosphatidylcholine | 40 g |
| Sorbitan oleate | 10 g |
| Jaguar C13S | 3 g |
| Active principle (for example permethrin) | 5 g |
| Water | 22 g |
| Mineral oil | 20 g |

The constituents are mixed at room temperature, being introduced in the following order: lecithin, cationic polymer, sorbitan oleate, active principle, water and then mineral oil. A homogeneous paste is obtained.

This paste can easily be dispersed in a mineral oil at a concentration of 10% to give a dispersion of vesicles encapsulating the active agent, the viscosity being adapted to use by deposition on the animal's back. As in Example 7, the dispersion needs to be shaken by hand before use in order to produce a perfect suspension.

Such a preparation, based on multilamellar vesicles encapsulating the active agent, has the advantages of the persistence of the active agent associated with the adhesion phenomenon, and also avoids systemic penetration of the active agent into the epidermis by virtue of the cationic charge on the vesicles. It is therefore particularly suitable for all active agents which have a local action on animals' fur.

Example 9
Moisturizing Formulation for Lipstick

The introduction of a hydrophilic moisturizer into a lipstick based on castor oil and beeswax, i.e. strongly hydrophobic, presents insurmountable technical problems. Using the multilamellar vesicles according to the invention makes it possible to solve this problem and provides the adhesion effect, and hence the persistence effect, of the moisturizer on the lips.

The vesicles are prepared from the following formulation:

| | |
|---|---|
| Sucrose tristearate | 30% |
| Glycerol | 60% |
| Jaguar C13S | 1% |
| Water | 9% |

All the constituents are crudely mixed at room temperature and the temperature is then raised to 70° C., with continued vigorous stirring. When the mixture is homogeneous, it is slowly cooled to room temperature, with continued moderate stirring. The product is in the form of a very firm paste.

This paste disperses readily in castor oil, which is then used to prepare the lipstick base according to a traditional formulation. It is thus possible to introduce up to 10% of vesicles into the lipstick, corresponding to 6% of glycerol, without degrading the cosmetic qualities of the product.

What is claimed is:

1. Method of making a product adhere to a surface, comprising bringing into contact with said surface a composition in which said product is incorporated in substantially spherical, multilamellar vesicles, with a diameter of between 0.1 and 100 μm, and comprising concentric membranes based on at least one surfactant and separated by a solvent medium, each of said vesicles having an onion-like structure comprising a succession of concentric bi-layers extending from each vesicle center to its periphery, and containing therein at least one cationic agent, resulting in the vesicles carrying a positive overall charge.

2. Method according to claim 1, wherein said surface has a negative charge.

3. Method according to claim 1, wherein said surface comprises a natural or artificial fiber or an assembly of fibers.

4. Method according to claim 1 wherein said surface is a biological surface.

5. Method of treatment of a human or animal body, making it possible to increase persistence of an active agent on a treated part of the body, comprising applying, to said treated part of the body, a composition in which said active agent is incorporated in substantially spherical, multilamellar vesicles, with a diameter of between 0.1 and 100 $\mu$m, and comprising concentric membranes based on at least one surfactant and separated by a solvent medium, each of said vesicles having an onion-like structure comprising a succession of concentric bi-layers extending from each vesicle center to its periphery, and containing therein at least one cationic agent, resulting in the vesicles carrying a positive overall charge.

6. Method according to claim 1, wherein said membranes comprise an effective amount of at least one cationic surfactant as said cationic agent for imparting a positive charge to said vesicles.

7. Method according to claim 6, wherein said cationic surfactant is selected from the group consisting of quaternary ammonium compounds, amines, amine salts or amides which can be protonated under the pH conditions of use of said composition, betaine or amino acid derivatives under pH conditions which render them cationic, imidazoline derivatives and quaternized dialkyl esters.

8. Method according to claim 1, wherein said vesicles comprise at least one encapsulated product having a cationic charge in an amount which is effective for imparting a cationic charge to said vesicles.

9. Method according to claim 8, wherein said encapsulated product is a cationic polymer.

10. Method according to claim 9, said cationic polymer is selected from the group consisting of polysaccharide derivatives, cationic protein hydrolyzates, polyamine derivatives, polyamino acids under pH conditions where they are cationic, polyethylene imine, quaternary derivatives of polyvinylpyrrolidone (PVP) and copolymers of quaternized polyvinylpyrrolidone and hydrophilic polymers, polyquaternium compounds and chitin derivatives.

11. Method according to claim 1, wherein said multilamellar vesicles contain from 0.01 to 10% by weight of said vesicles of at least one compound of cationic character.

12. Pharmaceutical composition for topical treatment of a human or animal body, comprising at least one active agent incorporated in substantially spherical, multilamellar vesicles, with a diameter of between 0.1 and 100 $\mu$m, and comprising concentric membranes based on at least one surfactant and separated by a solvent medium, each of said vesicles having an onion-like structure comprising a succession of concentric bi-layers extending from each vesicle center to its periphery, and containing therein at least one cationic agent, resulting in the vesicles carrying a positive overall charge.

13. Method according to claim 1, additionally comprising preparing said composition by a method comprising the steps of:

preparing a lamellar liquid crystal phase based on at least one surfactant comprising said cationic agent and, optionally, a product to be fixed or an active agent other than said cationic agent;

applying a shearing stress to said lamellar liquid crystal phase to form said vesicles; and incorporating said vesicles into an appropriate medium.

* * * * *